United States Patent [19]

Crouthamel

[11] Patent Number: 5,049,580

[45] Date of Patent: Sep. 17, 1991

[54] TREATMENT OF INFLAMED SKIN CONDITIONS INCLUDING POISON IVY AND POISON SUMAC, INSECT BITES AND ACNE

[75] Inventor: Gary Crouthamel, Freeport, N.Y.

[73] Assignee: Total Leather Care, Inc., Oceanside, N.Y.

[21] Appl. No.: 565,938

[22] Filed: Aug. 13, 1990

Related U.S. Application Data

[63] Continuation-in-part of Ser. No. 439,261, Nov. 20, 1989, abandoned.

[51] Int. Cl.$^5$ ............................................. A61K 31/40
[52] U.S. Cl. ................................... 514/424; 514/862; 514/867
[58] Field of Search ...................... 514/424, 862, 867

[56] References Cited

U.S. PATENT DOCUMENTS 4,039,664 8/1977 Stoughton et al. ................ 424/180

*Primary Examiner*—Leonard Schenkman
*Attorney, Agent, or Firm*—Sheldon Palmer

[57] ABSTRACT

Inflamed skin conditions caused by plants belonging to the same genus, namely, Toxicodendron and in particular, poison ivy or poison oak (*T. radicans*), poison sumac (*T. vernix*), insect bites and acne, all of which are characterized by the presence of an oily exudate of either external or bodily origin are treated by the topical applications of N-methylpyrrolidone to affected areas of the body. The N-methylpyrrolidone can be applied per se, or in a solution or dispersion thereof in one or more pharmacologically compatible carriers.

15 Claims, No Drawings

5,049,580

TREATMENT OF INFLAMED SKIN CONDITIONS INCLUDING POISON IVY AND POISON SUMAC, INSECT BITES AND ACNE

CROSS-REFERENCE TO RELATED APPLICATIONS

This is a continuation-in-part of co-pending application Ser. No. 07/439,261; filed Nov. 20, 1989, now abandoned.

BACKGROUND OF THE INVENTION

1. Field of the Invention

The present invention relates to a method for the treatment of numerous skin inflammation diseases which are characterized, or have associated therewith, an oily exudate of either external or bodily origin. The method comprises topically treating the affected skin area with N-methylpyrrolidone, also known as N-methyl-2 pyrrolidone.

2. The Prior Art

N-methylpyrrolidone is a known commercially available substance sold e.g., under the brand name M-Pyrol® (GAF Corporation). It is not considered, under the Federal Hazardous Substance Act to be a toxic substance.

The discomfort of persons who have contacted poison ivy, oak or any of the poison sumacs is well known. Many topical treatment methods have heretofore been used, the most common method being treatment with calamine lotion or the like. However, to date, there has been no really satisfactory topical treatment.

In general, the topical treatments of poison ivy, oak and sumac, result in continued oozing of the affected area which results in spreading the condition. The oozing of the blisters not only results in spreading of the infection, but also causes considerable discomfort. Moreover, numerous kinds of insect bites, including those of mosquitoes, bees, wasps, hornets, flies and ants also result in inflammation which is sometimes quite severe and on occasion fatal and which also are characterized by swelling and blistering including rupturing of the blisters and an oozing of an oily inflammatory exudate. Similar symptoms frequently characterize the onset of acne.

SUMMARY OF THE INVENTION

It is an object of the present invention to provide, and in one aspect thereof the invention provides methods for the treatment of poison ivy, oak and sumac as well as for other skin inflammatory conditions caused by insect bites (bees, wasps, mosquitos, hornets, flies and ants) and acne.

It is another object of the invention to provide, and in another aspect thereof, the invention provides methods for the topical treatment of the foregoing conditions which in a very short time by way of a single or several applications results in complete drying of all of the blisters or sacs which characterize these conditions and thus to prevent oozing and spreading thereof.

With the above objects in view, the invention comprises topically applying to an area of the body infected by poison ivy, oak, sumac or the site of an inset bite or acne an effective amount of N-methylpyrrolidone.

In accordance with one embodiment of the invention, the N-methylpyrrolidone is applied at 100% concentration to the affected areas of the skin; that is, at full strength.

In accordance with a further embodiment of the invention, the N-methylpyrrolidone can be dispersed in any compatible liquid such as water, alcohols, including ethanol or isopropanol and vegetable oils and in this manner, applied to the affected area of the skin.

As indicated, the N-methylpyrrolidone can be used at 100% concentration (full strength). However, concentrations as low as 1% or even less can be used. Generally, it is preferred to use concentrations of at least 10%.

Even though the N-methylpyrrolidone is preferably present in amounts of at least 10%, in actuality, it can be used at concentration levels as low as 1% because it is not an azeotropic material. That is, even if a composition containing 1% N-methylpyrrolidone and 99% ethanol were to be topically applied, as the ethanol evaporates off the skin (as it will do), the active material, i.e., N-methylpyrrolidone will remain behind on the skin and its therapeutic effects will be achieved in any event.

Compositions containing the N-methylpyrrolidone, e.g. aqueous solutions or alcoholic solutions thereof, can be used as such. It is also possible for such compositions to include up to about 1% by weight of a topical anesthetic such as benzocaine to relieve the pain of the affected area. It is also possible and even desirable to include humectants such as glycol, glycerine and polyethylene glycol to moisturize the skin.

Preferred compositions for use in accordance with the methods of the present invention contain 30-90% of N-methylpyrrolidone, preferably 30-50%. The N-methylpyrrolidone in these compositions is preferable mixed with water in an amount of 10-70%. As indicated, such compositions can contain a topical anesthetic such as benzocaine, e.g. in amounts of 1-10%, preferably about 1% and a humectant as defined above in an amount of 5-10%. These amounts, however, may vary considerably.

DESCRIPTION OF PREFERRED EMBODIMENTS

Example 1

A composition for the treatment of poison ivy or poison sumac is prepared by mixing:
Water: 60%
N-methylpyrrolidone: 30%
Glycerine: 10%.

This composition can be applied to an area of a person suffering from poison ivy, oak or sumac by means of a cotton swab or the like and permitted to dry. The application is continued throughout the day. Generally, only a second application is required. After about four hours duration, the result of two applications is substantially complete drying of all of the sacs and blisters of the poison ivy or poison sumac. By the next day, the entire affected area becomes patches of dry skin. One further application, if desired may be made. After these applications, the condition heals rapidly and no longer spreads. The healing is complete within one week.

Example 2

A composition is prepared as follows:
Water: 15%
N-methylpyrrolidone: 70%
Glycerine: 12%
Benzocaine: 3%

The above composition may be utilized in the same way as the composition of Example 1. There is the added advantage of lessened pain because of the topical anesthetic.

Example 3

N-methylpyrrolidone, at 100% concentration was applied to areas of the skin grossly affected by poison ivy. The patient had numerous affected areas over both arms consisting of large blisters which were oozing and spreading. The N-methylpyrrolidone was applied with cotton swabs and allowed to remain on the areas causing a drying action which was noticeable within one hour.

This continued throughout the day and a second application was then made. After four hours duration, the result of the two applications was a substantially complete drying of all sacs of the affected areas. By the next day, the entire affected areas were then patches of dry skin.

The condition healed rapidly with no further spreading and with total recovery within less than one week.

Example 4

This example represents the results of a number of separate applications of N-methylpyrrolidone at full strength (100%), at 30% (Example 1) and 15% (Example 2) to different patients who had previously been bitten by one or more insects including bees, wasps, hornets, mosquitos and the like using the procedures described in Examples 1 and 3. In all cases the inflammations and oozing exudates typically associated with such insect bites all were cleared up very quickly; in most cases, within one day.

While the invention has been described in connection with specific compositions and modes of treatment, it is apparent that variations and modifications of the invention can be made without departing from the spirit or scope thereof.

Having described my invention, what I desire to secure by Letters Patent and hereby claim is:

1. A method of treating an inflamed skin condition which has associated with it an oily exudate of either external or bodily origin, said method comprising topically applying to an inflamed affected area of the skin, a therapeutically effective amount of N-methylpyrrolidone.

2. A method according to claim 1 wherein the inflamed skin condition is poison ivy, poison sumac, poison oak, an insect bite or acne.

3. A method according to claim 2 wherein the insect bite is a bite from a mosquito, bee, wasp, hornet, fly or ant.

4. A method according to claim 1 wherein after topical applications the treated area of the skin is allowed to dry and the application is repeated as necessary.

5. A method of treating poison ivy and poison sumac, which comprises topically applying to an area of the body affected by the same, a poison ivy or poison sumac effective amount of N-methylpyrrolidone.

6. A method according to claim 5 wherein after application the area is permitted to dry and the application is repeated as necessary.

7. A method according to claim 5 wherein said application is by way of a liquid in which the amount of N-methylpyrrolidone is up to 90% by weight.

8. A method according to claim 5 wherein said application is by way of a liquid in which the amount of N-methylpyrrolidone is up to 70% by weight.

9. A method according to claim 5 wherein said application is by way of a liquid in which the amount of N-methylpyrrolidone is up to 50% by weight.

10. A method according to claim 5 wherein said application is by way of a liquid in which the amount of N-methylpyrrolidone is up to 25% by weight.

11. A method according to claim 5 wherein the N-methylpyrrolidone is topically applied in the form of a composition comprising a poison ivy or poison sumac effective amount of N-methylpyrrolidone distributed in a pharmacologically compatible carrier, and including a humectant.

12. A method according to claim 11 wherein said humectant is glycerine.

13. A method according to claim 11 wherein the composition also includes a topical anesthetic.

14. A method according to claim 13 wherein said topic anesthetic is benzocaine.

15. A method according to claim 13 wherein said humectant is glycerine.

* * * * *